(12) United States Patent
Hillbratt et al.

(10) Patent No.: US 8,144,909 B2
(45) Date of Patent: Mar. 27, 2012

(54) CUSTOMIZATION OF BONE CONDUCTION HEARING DEVICES

(75) Inventors: Martin Evert Gustaf Hillbratt, Vastra Gotaland (SE); Gunnar Kristian Asnes, Molndal (SE)

(73) Assignee: Cochlear Limited, Macquarie University, NSW (AU)

( * ) Notice: Subject to any disclaimer, the term of this patent is extended or adjusted under 35 U.S.C. 154(b) by 729 days.

(21) Appl. No.: 12/190,424

(22) Filed: Aug. 12, 2008

(65) Prior Publication Data

US 2010/0041940 A1 Feb. 18, 2010

(51) Int. Cl.
*A61B 5/00* (2006.01)

(52) U.S. Cl. ........ 381/326; 600/559; 600/544; 381/322; 702/189

(58) Field of Classification Search .............. 381/23.1, 381/60, 58, 312, 314, 323; 702/57; 600/559, 600/544

See application file for complete search history.

(56) References Cited

U.S. PATENT DOCUMENTS

| | | | |
|---|---|---|---|
| 3,809,829 A | 5/1974 | Vignini et al. | |
| 4,498,461 A | 2/1985 | Hakansson | |
| 4,904,233 A | 2/1990 | Hakansson et al. | |
| 5,323,468 A | 6/1994 | Bottesch | |
| 5,800,475 A | 9/1998 | Jules | |
| 5,805,571 A * | 9/1998 | Zwan et al. | 370/249 |
| 5,913,815 A | 6/1999 | Ball et al. | |
| 6,602,202 B2 * | 8/2003 | John et al. | 600/559 |
| 6,643,378 B2 * | 11/2003 | Schumaier | 381/326 |
| 6,840,908 B2 | 1/2005 | Edwards et al. | |
| 7,018,342 B2 | 3/2006 | Harrison et al. | |
| 7,074,222 B2 | 7/2006 | Westerkull | |
| 2004/0078057 A1 | 4/2004 | Gibson | |
| 2004/0082980 A1 | 4/2004 | Mouine et al. | |
| 2004/0204921 A1 * | 10/2004 | Bye et al. | 702/189 |
| 2005/0171579 A1 * | 8/2005 | Tasche et al. | 607/57 |
| 2006/0018488 A1 | 1/2006 | Viala et al. | |
| 2006/0287689 A1 | 12/2006 | Debruyne et al. | |
| 2011/0022119 A1 | 1/2011 | Parker | |
| 2011/0026721 A1 | 2/2011 | Parker | |
| 2011/0026748 A1 | 2/2011 | Parker | |

FOREIGN PATENT DOCUMENTS

| | | |
|---|---|---|
| WO | WO 91/12783 | 9/1991 |
| WO | 9907311 | 2/1999 |
| WO | 2005/029915 A1 | 3/2005 |
| WO | 2005029915 | 3/2005 |

(Continued)

OTHER PUBLICATIONS

F.M. Vaneecloo et al., "Réhabilitation prothétique B.A.H.A des cophoses unilatérales", Annales D'oto-Laryngies et de Chirurgie Cervicofaciale, vol. 117, No. 6, Dec. 2000, pp. 410-417, 8 pages.

(Continued)

*Primary Examiner* — Steven Loke
*Assistant Examiner* — David Goodwin
(74) *Attorney, Agent, or Firm* — Kilpatrick, Townsend & Stockton, LLP.

(57) ABSTRACT

The present invention relates to recipient customization of a bone conducting hearing device. Customization of the bone conducting hearing device may include attaching the bone conducting hearing device to a recipient, establishing communication between the hearing device and an external device, generating at least one control setting with the external device, and storing the at least one control setting in a memory device in the hearing device.

20 Claims, 6 Drawing Sheets

FOREIGN PATENT DOCUMENTS

| | | |
|---|---|---|
| WO | 2005122887 | 12/2005 |
| WO | 2007140367 | 12/2007 |
| WO | 2009124005 | 10/2009 |
| WO | 2009124008 | 10/2009 |
| WO | 2009124010 | 10/2009 |
| WO | 2010017579 | 2/2010 |

OTHER PUBLICATIONS

Michael Nolan et al., "Transcranial attenuation in bone conduction audiometry", The Journal of Laryngology and Otology, Jun. 1981, vol. 95, pp. 597-608, 12 pages.

European Patent Application No. 02 736 403.3, Office Communication mailed on Oct. 17, 2008. 6 Pages.

European Patent Application No. 02 736 403.3, Office Communication mailed on Apr. 27, 2009. 4 Pages.

European Patent Application No. 02 736 403.3, Office Communication mailed on Apr. 13, 2010. 6 Pages.

International Application No. PCT/SE02/01089, International Search Report mailed on Oct. 1, 2002. 3 Pages.

International Application No. PCT/SE02/01089, International Preliminary Examination Report mailed on Oct. 6, 2003. 5 Pages.

International Search Report issued by the International Searching Authority in connection with International Patent Application No. PCT/AU2009/001010, mailed Nov. 25, 2009 (4 pages).

International Search Report issued by the International Searching Authority in connection with International Patent Application No. PCT/US2009/038879, mailed May 22, 2009 (1 page).

Written Opinion issued by the International Searching Authority in connection with International Patent Application No. PCT/US2009/038879, mailed May 22, 2009 (4 pages).

International Search Report issued by the International Searching Authority in connection with International Patent Application No. PCT/US2009/038884, mailed Jun. 22, 2009 (1 page).

Written Opinion issued by the International Searching Authority in connection with International Patent Application No. PCT/US2009/038884, mailed Jun. 22, 2009 (5 pages).

International Search Report issued by the International Searching Authority in connection with International Patent Application No. PCT/US2009/038890, mailed May 29, 2009 (1 page).

Written Opinion issued by the International Searching Authority in connection with International Patent Application No. PCT/US2009/038890, mailed May 29, 2009 (6 pages).

International Preliminary Report on Patentability issued by International Preliminary Examining Authority in connection with International Patent Application No. PCT/US2009/038890, mailed Apr. 15, 2010 (8 pages).

Henry et al., "Bone Conduction: Anatomy, Physiology, and Communication," Army Research Laboratory, May 2007 (206 pages).

* cited by examiner

FIG. 6

CUSTOMIZATION OF BONE CONDUCTION HEARING DEVICES

BACKGROUND

1. Field of the Invention

The present invention generally relates to bone anchored hearing devices, and more particularly, to customization of bone anchored hearing devices.

2. Related Art

To improve hearing for many hearing impaired individuals, hearing aids that amplify sound to stimulate the eardrum are often utilized. When using these types of hearing prostheses the auditory meatus is generally completely or substantially occluded by a hearing plug or by the hearing aid itself to prevent undesirable acoustic feedback. These plugs may cause the recipient discomfort, eczema, chronic inflammations and/or chronic infections in the auditory canal.

Additionally, there are other types of hearing prostheses that improve hearing for hearing impaired individuals. These types of devices include bone conducting or bone anchored hearing devices ("bone conducting devices"), which transmit sound information to a recipient's inner ear via vibration of the skull bone. When anchored to the bone, such bone conducting devices are generally connected to an implanted titanium screw installed and osseointegrated in the mastoid. The sound is then transmitted via the skull bone to the cochlea (inner ear). This type of bone conducting device generally allows the recipient to perceive sound regardless of whether there is disease or missing parts in the middle ear.

Traditionally, bone conducting devices are problematic since customization of the hearing device for each recipient, if even possible, is done manually, and optimum settings for an individual are difficult to obtain. For example, if a recipient has difficulty perceiving sound, the recipient may only be able to adjust the overall volume of the device. Further, recipient's hearing abilities generally vary significantly, making setting of the bone conducting device complicated. For example, many recipients hear relatively well at some frequencies, but very poorly at others.

Still further, the sound conduction conditions (i.e., the body and head of the recipient, the bone anchored implant and the external hearing device) are different for each recipient, which makes pre-setting of the hearing device impracticable. For example, resonance frequencies typically occur at different frequencies for each recipient.

SUMMARY

The present invention relates to a method for recipient customization of a bone conducting hearing device. In one embodiment, the method comprises the steps of attaching the bone conducting hearing device to a recipient, establishing communication between the hearing device and an external device, generating at least one control setting with the external device, and storing the at least one control setting in a memory device in the hearing device.

The present invention also relates to a bone conducting hearing device. In one embodiment, the hearing device comprises a microphone configured to generate an electrical signal, a signal processing unit configured to amplify the electrical signal from the microphone, a vibrator configured to convert the amplified electrical signal into vibrations, an interface configured to allow the hearing device to communicate with an external control device, and at least one memory unit for storing control data for controlling the signal processing unit, wherein the interface is adapted to receive control signals from the external control device for generating vibrations in the vibrator at a plurality of predetermined frequencies, and to receive control settings for the signal processing unit for storing in the memory unit to reproduce the vibrations at each predetermined frequency.

The present invention also relates to a computer readable medium including computer software programmed to execute a method for recipient customization of bone conducting hearing devices. The method comprises the steps of establishing communication between the bone conducting hearing device and an external control device, determining measurement data related to the recipient's ability to perceive sound at a predetermined frequency, generating at least one control setting for a signal processing unit based on the bone conduction threshold, and transmitting the at least one control setting includes transmitting the a plurality of control settings to the hearing device.

These and other aspects of the invention will be apparent from and elicited with reference to the embodiments described hereinafter.

BRIEF DESCRIPTION OF THE DRAWINGS

Embodiments of the present invention are described herein with reference to the accompanying drawings; in which.

DETAILED DESCRIPTION

Aspects of the present invention are generally directed to improving the sound percept of a bone conduction hearing device ("hearing device") for a recipient. When attached to the recipient, the hearing device may have its control settings altered to allow a recipient improved sound percept at least one frequency. The control settings may be altered or set using an external device such as a fitting system, PDA, computer, mobile phone, etc.

The external device may alter or set the intensity level at which a particular recipient is to experience a desired percept for a variety of frequency channels. To achieve the desired percept, the external device determines the mV output that evokes the desired percept in the recipient. The external device may repeatedly present acoustic targets to the hearing device and increment or decrement the corresponding mV output until the recipient experiences the desired percept in response to the acoustic target. These output levels are stored in the hearing device for subsequent operations. Additionally, the acoustic targets may be set by the recipient, an audiologist or any other third party in an acoustic domain environment. In such an acoustic domain environment, it is not required to have detailed knowledge of how electrical stimulation signals are defined, generated and/or controlled to set the control settings for the hearing device.

Figure 1:
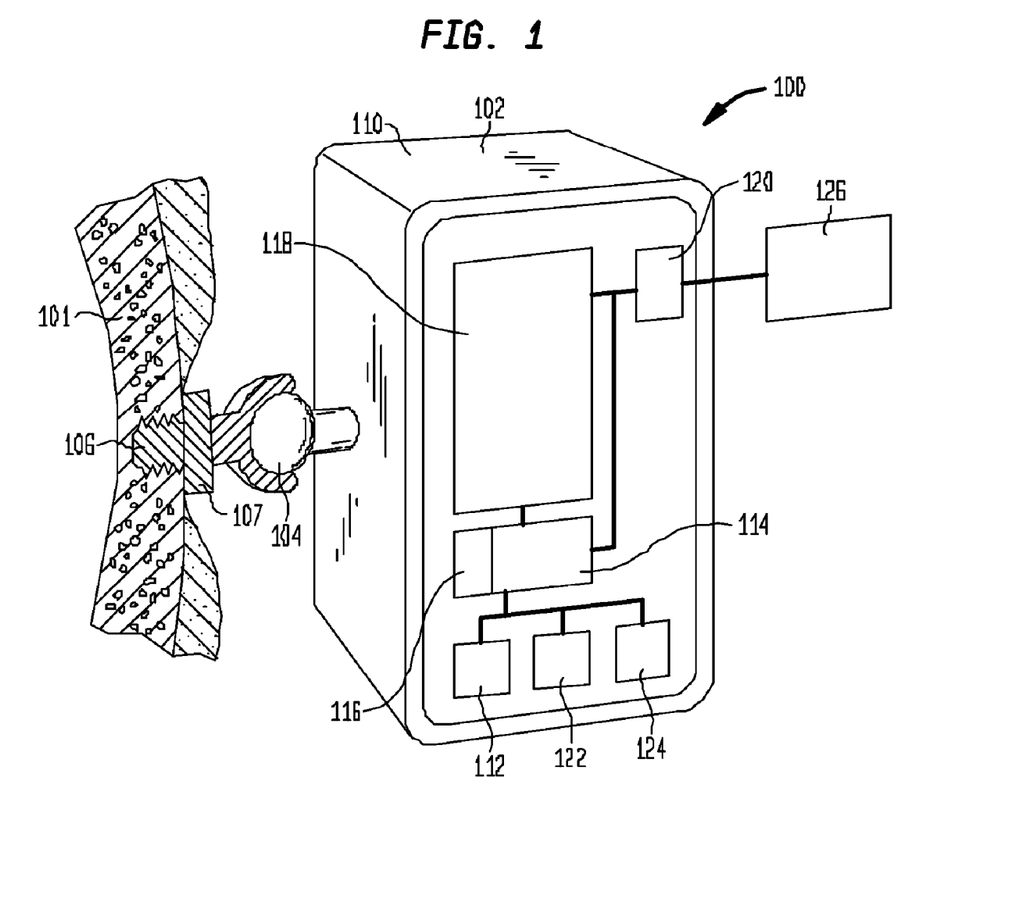
FIG. 1 is a schematic overview of a bone-anchored hearing device in accordance with an embodiment of the present invention.

FIG. 1 illustrates a bone-anchored hearing device ("hearing device") 100, which transmits sound information to a recipient's inner ear via the skull bone 101. The hearing device includes a detachable body portion 102, a coupling arrangement or portion ("coupling arrangement") 104 and an implantable fixture or anchor ("fixture") 106. The fixture is preferably implanted and osseointegrated in the bone behind the external ear. The detachable body portion may then be coupled to the fixture using coupling arrangement 104, allowing sound to be transmitted via the skull bone to the cochlea (inner ear).

In one embodiment, fixture 106 is anchored into the mastoid bone behind the outer ear; however, the fixture may be implanted under skin within muscle and/or fat or in any other suitable manner. In one embodiment, fixture 106 is a titanium fixture of the type described in U.S. Pat. No. 7,074,222 (the "'222 patent"), which is hereby incorporated by reference; however, the hearing device 100 may be anchored in any suitable manner or position and is not limited to or by the disclosure or the '222 patent. Fixture 106 is preferably made of titanium, since titanium may be integrated into the surrounding bone tissue (i.e., osseointegration); however, the fixture may be any suitable material or combination of materials.

Preferably, as stated above, the detachable body portion 102 is connected to fixture 106 via coupling arrangement 104. In some embodiments, coupling arrangement 104 may be a bayonet coupling or mechanical spring coupling; however the coupling arrangement may be any suitable coupling. The hearing device may include, in addition to the titanium fixture, a spacer element or skin penetrating member 107 which may be connected to the bone anchored titanium fixture by a spacer screw or in any other suitable manner.

In one embodiment, the detachable portion includes housing 110, which is preferably formed from plastic, but may be formed from any suitable material and be any suitable shape or size. The detachable portion 102 preferably includes a microphone 112 (or other suitable sound input device), an electronic unit 114, a battery 116, a vibrator 118, a first memory unit 122, a second memory unit 124 and a data interface 120. It is noted that the hearing device 100 does not need to include each of these elements and may include all, some or none and may include any additional desired elements.

In one embodiment, microphone 112 acquires sound and generates a signal which is sent to the electronic unit 114. Preferably, electronic unit 114 is battery powered and may be a signal processing unit that amplifies the signal from the microphone 112. In one embodiment, the electronic unit 114 is equipped with an electronic filtering device arranged to reduce the amplification in the signal processing chain of the hearing device; however, the electronic unit 114 may be equipped with any suitable components and does not necessarily include a filtering unit. The amplified signal is supplied to a vibrator 118 which converts the electrical signal into vibrations which are then transferred to the skull bone via the titanium fixture 106.

In one embodiment, the hearing device 100 includes at least one memory unit, in communication with, connected to or integrated within the electronic unit 114. Preferably, the memory unit includes a first memory unit 122 for short-term storage, such as a RAM-memory device, and a second memory unit 124 for long-term storage, such as an EEPROM, flash or other suitable non-volatile memory device; however, it is noted that the hearing device may include any number and/or type of memory units. The memory units are configured to store control data for controlling the signal processing in the electronic unit 114.

In one embodiment, the hearing device includes a data interface 120 that enables data communication between the hearing device (e.g., the electronic unit 114) and an external control device or system ("external device") 126. As stated above, the external device may be external device such as a fitting system, PDA, computer, mobile phone, or any other suitable device. Preferably, the interface allows two-way or bidirectional communication. That is, interface data may be sent from both the electronic unit 114 and the external device 126. For example, in one embodiment, the interface may be adapted to receive control signals from the external device for generating vibrations in the vibrator at predetermined frequencies, and receive control settings for the electronic unit for storing in the memory unit. In some embodiments, however, the interface is a one way interface, allowing only data to be forwarded from the external device 126 to the hearing device. In other embodiments, communication is a one way interface with data being forwarded from the hearing device to any type of receiving device. The data may include measured control signals or any type of status information or other suitable data. This information may be used to merely monitor the hearing device or be used with a control device that may be a separate device or be integrated into the hearing device or be any other suitable device.

Figure 2:
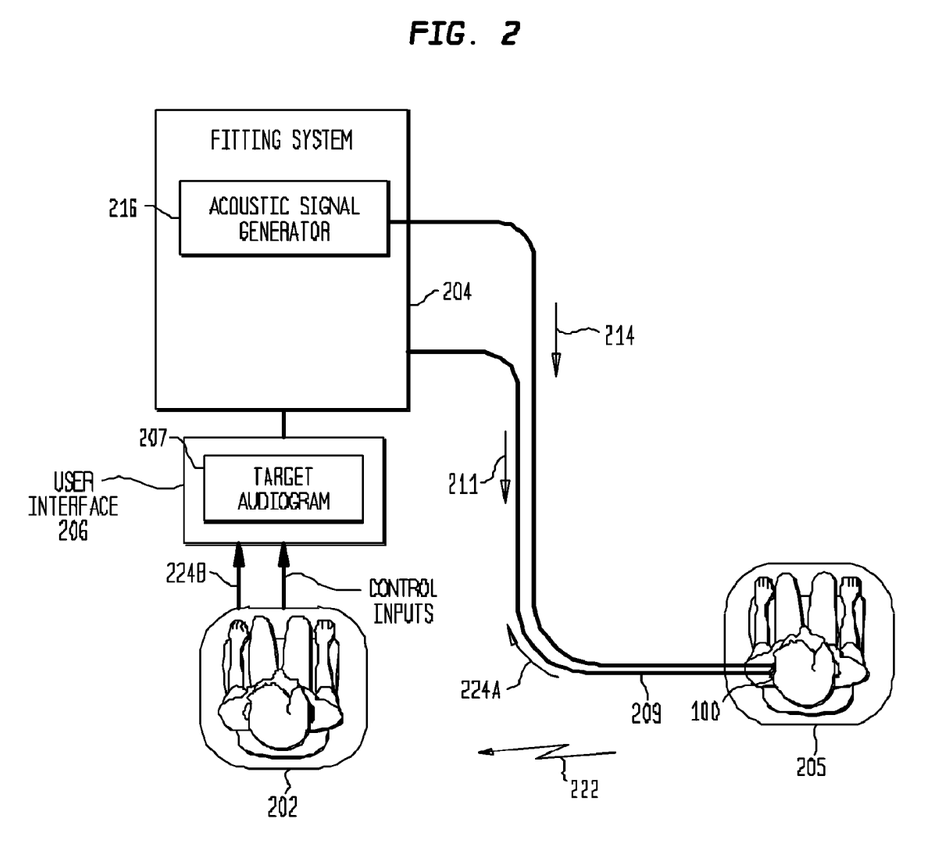
FIG. 2 is a schematic diagram of an exemplary external device in which control settings for a bone conduction hearing device are generated and stored in the hearing device.

FIG. 2 is a schematic diagram in which hearing device 100 (FIG. 1) has its control settings altered by a third party 202 using an exemplary external control system or device ("external device") 204. Specifically, FIG. 2 illustrates a fitting system in which an audiologist sets or alters the control settings. It is noted however, that, as stated herein, the external device does not necessarily need to be a fitting system and may be any suitable external device and does not need to be operated by an audiologist, but may be operated by any suitable third party or the recipient 205. As described below, external device 204 permits a third party 202 who lacks detailed understanding of electrical stimulation to configure hearing device 100 (FIG. 1) for a recipient.

As shown in FIG. 2, third party 202 uses an external device 204 that includes interactive software and computer hardware to configure individualized recipient control settings, which are used for subsequent normal hearing device operations by electronic unit 114 (FIG. 1).

In accordance with the embodiments of FIG. 2, external device 204 includes an acoustic domain environment through which third party 202 specifies for a variety of frequency channels the intensity level at which a particular recipient is to experience a desired percept. As described below, for each of these acoustic targets, external device 204 determines the mV level that evokes the desired percept in the recipient 205.

In one embodiment, the acoustic domain environment presents fitting information or other data in the acoustic domain; that is, the data is presented as acoustic-based data which may be understood by a third party or is the form commonly used by audiologists to fit hearing aids. In one embodiment, the acoustic domain environment includes one or more graphs or plots displayed on a user interface 206 that illustrate frequency-gain relationships, such as a target audiogram 207 described in greater detail below with reference to FIGS. 5 and 6.

In one embodiment, for each of the acoustic targets, external device 204 determines the mV output level that evokes the desired percept in the recipient. This may be accomplished by having the external device 204 repeatedly present each acoustic target to the hearing device and increment or decrement the corresponding mV output level until recipient 205 experiences the desired percept in response to the acoustic target. These levels are included in the control settings and are stored in the memory for subsequent normal hearing device operations by that recipient.

In embodiments of the present invention, in the initial stage, a selected acoustic target is presented to hearing device 100. The selected acoustic target may be presented as an acoustic test signal 214 having the intensity and frequency of the acoustic target. In certain embodiments, this acoustic test signal 214 may be generated by acoustic signal generator 216. As shown, acoustic test signal 214 may be presented to the recipient via audio cable 218. Alternatively, acoustic test signal 214 may be presented by wireless transmission. In certain embodiments of the present invention, third party 202 presses a control button on user interface 206 to present acoustic test signal 214 to recipient 205.

Presentation of the selected acoustic target causes an electrical stimulation signal to be delivered to the hearing device via the data interface 120 (FIG. 1) at an output level corresponding to the selected acoustic target. The output level corresponding to the acoustic target specified is iteratively adjusted until presentation of the acoustic target evokes a desired percept.

Following presentation of the acoustic target, a determination is made as to whether the delivered stimulation signal evoked a desired percept. This determination is based on the response of recipient 205 to the stimulation. As shown in FIG. 2, the recipient's response may comprise verbal or non-verbal feedback 222 from recipient 205. In such embodiments, using feedback 222, third party 202 enters an indication at user interface 206 as to whether the desired percept was evoked. This indication is shown as measurement data 224A. Third party 202 may enter measurement data 224A using any one or combination of known methods, including a computer keyboard, mouse, voice-responsive software, touch-screen, retinal control, joystick, and any other data entry or data presentation formats now or later developed. Measurement data 224A may simply indicate whether or not recipient 205 heard a sound following presentation of the acoustic target. Alternatively, functions may be provided which permit third party 202 to indicate if a perceived sound was too loud or too soft. In another embodiment, measurement data 224B may be sent though communication link 209.

As described below in more detail with reference to FIG. 4, if a desired percept is not evoked by presentation of the acoustic target, then the mV output level corresponding to the selected acoustic target is adjusted. This process continues until presentation of an acoustic target evokes a desired percept.

Determination that the desired percept was evoked indicates that the output level then specified is the correct level which will cause the desired percept at the target intensity and frequency. This level, referred to herein as the default control setting, generated in the external device may be stored by external device 204 for later use in generating the recipient's control settings. The above process may be repeated until default control settings corresponding to all acoustic targets have been determined. After determination of default control settings corresponding to all desired acoustic targets, the default control settings are loaded into electronic unit 114 via the communication link 209, as indicated by arrow 211. Typically, the default control settings are stored in long term memory; however, they may be stored in short term memory, if desired. As described in greater detail below with reference to FIG. 4, further adjustments to the control settings may then be made to meet the listening requirements of the recipient.

Figure 3:
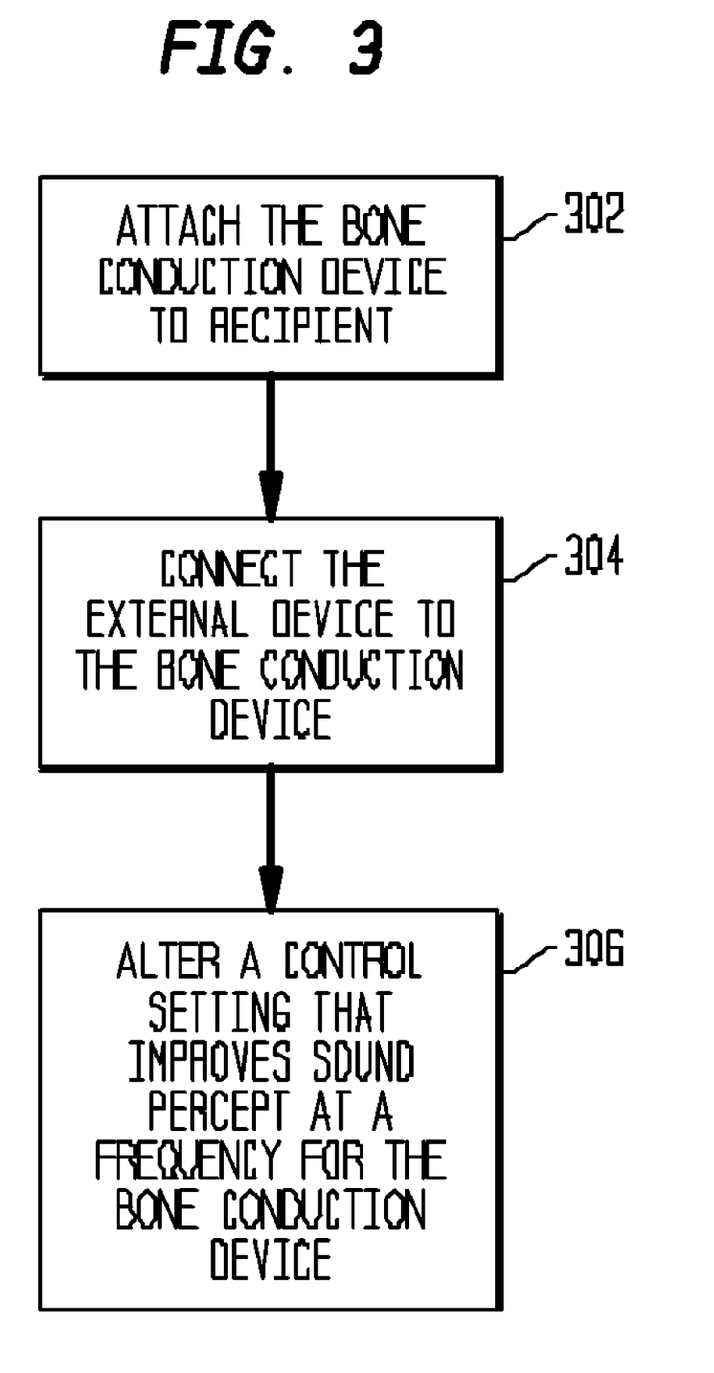
FIG. 3 is a high-level flow chart illustrating the customization of a bone anchored hearing device using an external device.

FIG. 3 is a high-level flow chart illustrating a method of altering the control settings of a bone conduction hearing device ("hearing device") according to one embodiment of the present invention. In the illustrative embodiments, at block 302 the hearing device is attached to the recipient. By attaching the hearing device to the recipient, the hearing device itself may provide the vibrations to the inner ear. When the vibrator in the hearing device is used, it is possible to measure the influence of the specific sound conduction conditions, such as resonance levels occurring in the hearing device, in the connection between the hearing device and the skull bone, or in the patients head.

At block 304, the external device is connected to the hearing device. As stated above, the external device may be coupled to the hearing device using wires, wirelessly or in any other suitable manner. At block 306 the external device transmits a control setting to the hearing device, altering the control settings for the hearing device to improve sound percept at a frequency for the recipient. In some embodiments, the control settings are based on the recipient's real world experience and/or the third party's experience with the device. For example, the recipient may find that volume adjustment is necessary for various or all frequencies. In one embodiment, the recipient would alter the control settings for various or all frequencies using external device 204. In another embodiment, the recipient could convey this information to a third party, who would then alter the control settings for the various or all frequencies using the external device.

As stated above, the control setting may be altered by storing commands in the memory that indicate an output of the electronic unit to the vibrator. For example, if the recipient determines that a decibel increase is necessary at a specific or plurality of frequencies, the control settings are altered or supplemented, which instruct the electronic unit to generate a higher mV output at the specific frequency or frequencies corresponding to the particular increase.

Figure 4:
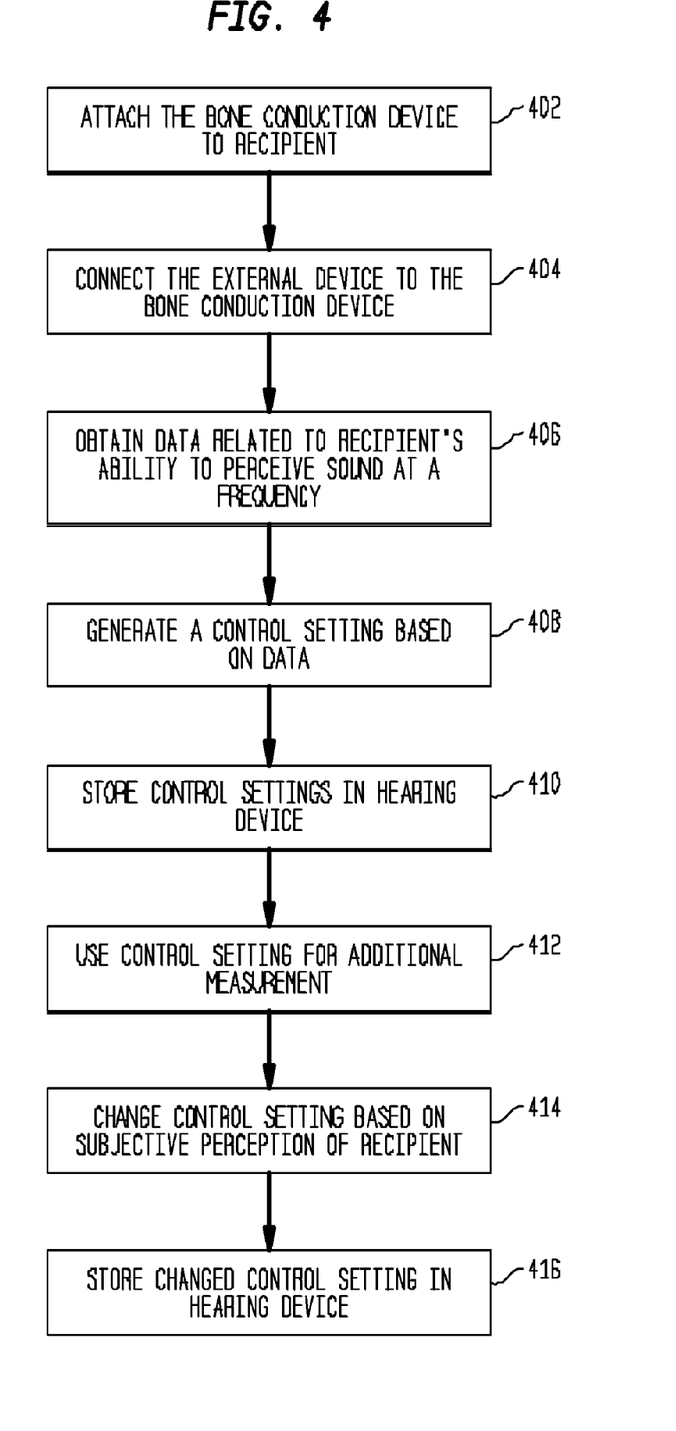
FIG. 4 is a detail-level flow chart illustrating operations that may be performed to determine customized control settings in accordance with embodiments of the present invention.

FIG. 4 illustrates a detail-level flow chart for customization of a bone anchored hearing device ("hearing device") according to one embodiment. As described above, at block 402 the hearing device is attached to the recipient, and at block 404, the external device is connected to the hearing device.

In block 406, measurement data may be obtained related to the recipient's ability to perceive sound at various frequencies when the hearing device is fitted to the recipient. In one embodiment, the measurement data may be related to bone conduction threshold levels at various frequencies. For example, audiogram data may be generated that indicates bone conduction threshold levels for the signal power at which the recipient is able to perceive sound at various frequencies. However, it is noted that the measurement data may be any level of percept at a specific frequency or range of frequencies for the recipient and does not necessary need to be the threshold level. Bone conduction threshold is typically the level where a stimulus or a change in stimulus to the bone is sufficient to produce a certain sensation or an effect (e.g., minimum level for the recipient to perceive a sound). The stimulus used is preferably a series of sinusoids, warble tone, noise or pure tones; however, the stimulus may be any suitable stimulus.

In one embodiment, the stimulus is generated using the external device in communication with the hearing device. The external device generates a signal that produces a desired output from the electronic unit. In one embodiment, the output is a predetermined mV output. This predetermined output vibrates the vibrator to illicit sound percept in the recipient.

Preferably, the vibrator in the hearing device is used to generate the vibrations; however, an external sound source or vibration source (not shown), controlled by the external device 204, may be used for generation of the measurement data. If an external vibration source is used, it is preferably coupled to the fixture 106 (FIG. 1). By coupling the external vibration source to the fixture 106, more accurate measurements may be generated for the recipient's bone conduction thresholds. Once the bone conduction thresholds are measured using the external vibration source, they are converted to the hearing device. Such conversion could be accomplished by using accelerometers to determine the relative compensation. That is, as one of ordinary skill in the art would understand, the vibration of the hearing device and the external vibration source could be measured using accelerometers at the same voltage and the difference is the compensation value. However, it is noted that, if desired, any external vibration source may be used. For example, a vibration device that is pressed against the skin or held between the teeth may be used.

As stated above, by using the vibrator in the hearing device, more accurate measurement data may be generated. For example, using the vibrator in the hearing device would allow measurement of the influence of the specific sound conduction conditions, such as resonance levels occurring in the hearing device, in the connection between the hearing device and the skull bone, or in the patients head. Further, as stated above, measurements based on the hearing device itself may eliminate the risk of conversion errors and the like (e.g., the compensation value using accelerometers).

Preferably, threshold level measurements for the recipient's hearing are acquired at least one different frequency, and preferably at least 10 different frequencies, however, these measurements may be obtained at any number of suitable frequencies. For example, the measurement at various frequencies may be performed as an audiogram, where the measurement is made at octave frequencies, and optionally also mid-octaves, between 125 and 8000 Hz. However, it is noted that the measurements may be made at any frequency or frequencies or within any frequency band or in any suitable manner.

In one embodiment, the recipient or third party may repeatably send signals to the hearing device at a specific frequency until the desired response from the recipient is obtained. During this procedure, the recipient indicates if a sound is perceived at a specific frequency. Such indication may be verbal, non-verbal or any desired indication. If the recipient does not perceive a sound, no indication is provided. If no indication is provided, the mV output is increased by a desired or predetermined level using the external device. This increase in mV output is continued until the recipient indicates that the sound is perceived or until a suitable level of sound percept is achieved. This indication is the measurement data.

Based on the measurement data, the external device at block 408 generates a default control setting for the electronic unit 114. In one embodiment, this default control setting increases the amplification at a frequency or multiple frequencies where the recipient's ability to perceive sound is reduced. In other embodiments, the control setting provides lower amplification at other frequencies.

In one embodiment, the control setting increases or decreases the mV output of the electronic device to generate a desired vibration of the vibrator in the hearing device. For example, if it is determined that the recipient requires a 6 dB increase to perceive sound at a specific frequency, a control setting is generated that instructs the electronic device to send the required mV output. Typically, a 6 dB increase requires doubling the mV output. The control setting may be stored in memory 122 if further enhancement is anticipated.

At block 410, the initial control settings indicating, for example, the threshold level for the recipient, may be stored in the memory unit of the hearing device as default control settings for subsequent use. The control setting may be stored automatically or manually or any combination thereof. For example, once the recipient indicates that sound is perceived, the third party may indicate such on the control panel and the control setting is automatically stored. In another embodiment, the third party or the recipient may have the choice of storing that control setting when the recipient indicates that the threshold has been met or not storing the control setting and storing a different value for percept at sound for that frequency.

To further enhance the recipient's perception, the control settings may be altered. The altering of the control settings may occur at the initial fitting of the hearing device or at a subsequent time. As illustrated in FIG. 4 at block 412, the stored default control settings are used to generate additional measurement data. The external device determines the control settings based on communication with the electronic device 114, and enables the alteration of the output of the electronic device. Based on the subjective perception of the recipient or on experience of the third party, as shown at block 414, the control settings may then be changed to match the subjective needs of the recipient. In some embodiments, the altered control settings are based on the recipient's real world experience and/or the third party's experience with the hearing device. For example, the recipient may find that volume adjustment is necessary for various or all frequencies. In one embodiment, the recipient would alter the control settings for various or all frequencies using external device 204. In another embodiment, the recipient could convey this information to a third party, who would then alter the control settings for the various or all frequencies using the external device. In another embodiment, the hearing device is configured to store related to sound in different environments. The third party or the recipient may access this data via the external device and download the data to the external device. Based on this data, the external device can generate new control settings that are stored in the memory unit. Thus, based on the third parties knowledge of an environment or real world situation, the third party could alter the control setting for that specific environment.

In one embodiment, the recipient may alter the control settings using a PDA or other portable device, such that the recipient adjusts the control setting in the real world environment. For example, if the recipient determines that it is difficult to perceive low frequency sound, the recipient may adjust a low frequency control setting using an external device such as a PDA while attempting to perceive the real world low frequency sound. In another embodiment, the PDA or other portable device is used to monitor and record the various frequencies or situations in which the recipient has reduced sound percept and such data may be downloaded into an external device that alters the control settings.

In one embodiment, the control settings may be altered by repeatedly increasing or decreasing the output of the electronic unit until the desired percept is reached. For example, if the third party or recipient indicates that the threshold level for a specific frequency is inadequate, the external device may increase the output of the electronic unit until the desired percept is reached. This measurement data may then be stored in the memory unit of the hearing device as a control setting for this frequency. This procedure may be repeated for all or some frequencies.

As illustrated in block 416, the personally adapted control settings may then be stored in the hearing device for subsequent use, replacing the previously stored default control setting. Additionally, the personally adapted control settings may merely be added to the hearing devices memory in addition to the default settings. When the final control settings have been obtained, these are preferably forwarded to the non-volatile memory 124 in the hearing device for subsequent use. Thus, the recipient runs no risk of loosing these settings during ordinary use of the hearing device, after the initial setting procedure, or after subsequent updates.

In one embodiment, a plurality of different control settings may be generated for use in different sound environments. In other words, the hearing device may have available control settings that alter the recipient's percept at the same frequency or frequency bands depending on the environment. In one embodiment, the different control settings are selectable on the hearing device. Thus, individual optimization is possible for various programs that are selectable by the recipient. For example, the recipient may select a program for indoor environments, a program for outdoor environments, a program for listening to electronic sound devices, such as MP3-players, or any other suitable environment. The control settings of each of these programs may be generated and stored separately as described above.

Figure 5:
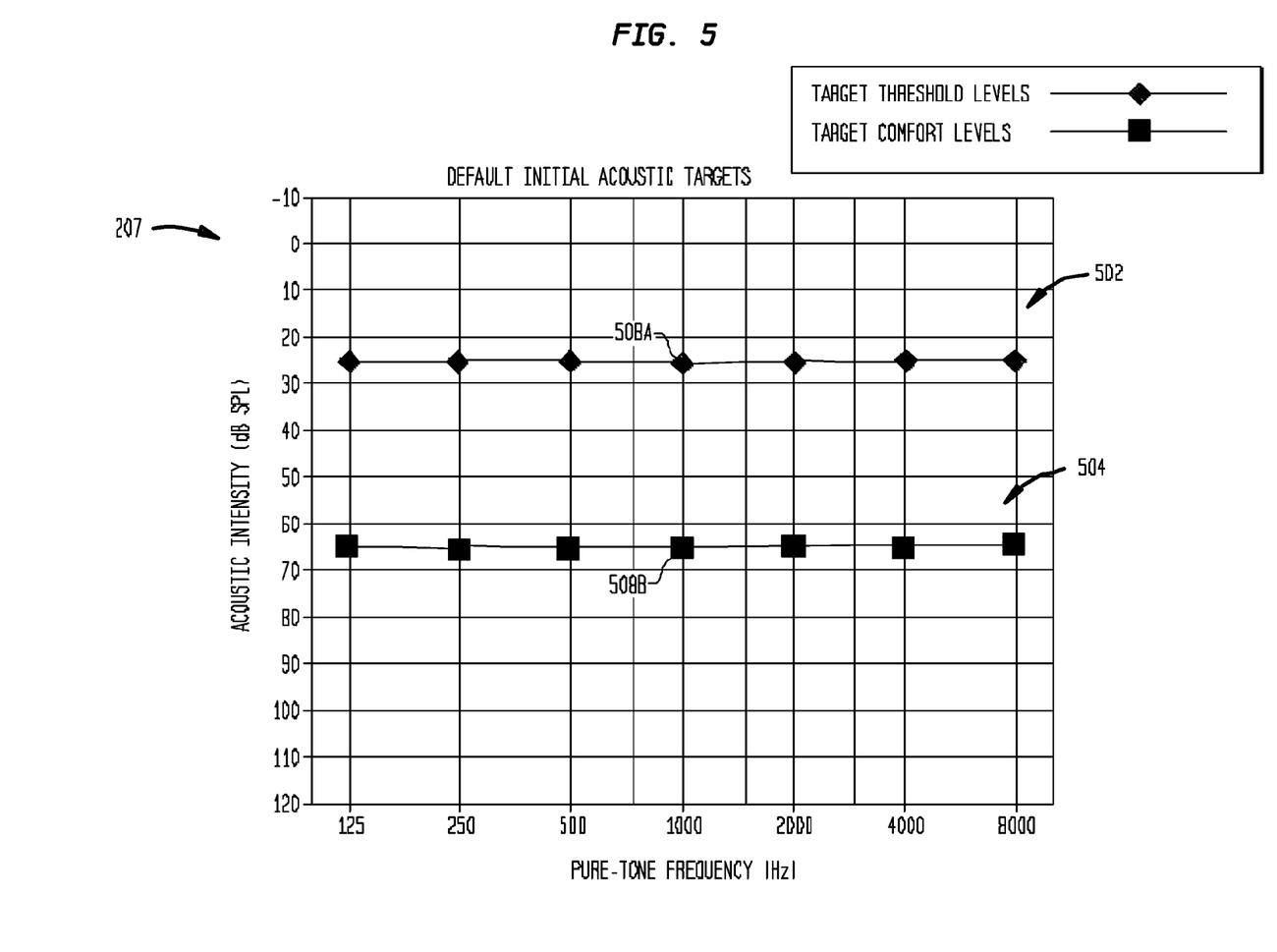
FIG. 5 is an exemplary target audiogram displayed to third party by the external device illustrated in FIG. 2 to graphically present default acoustic targets in accordance with embodiments of the present invention.
Figure 6:
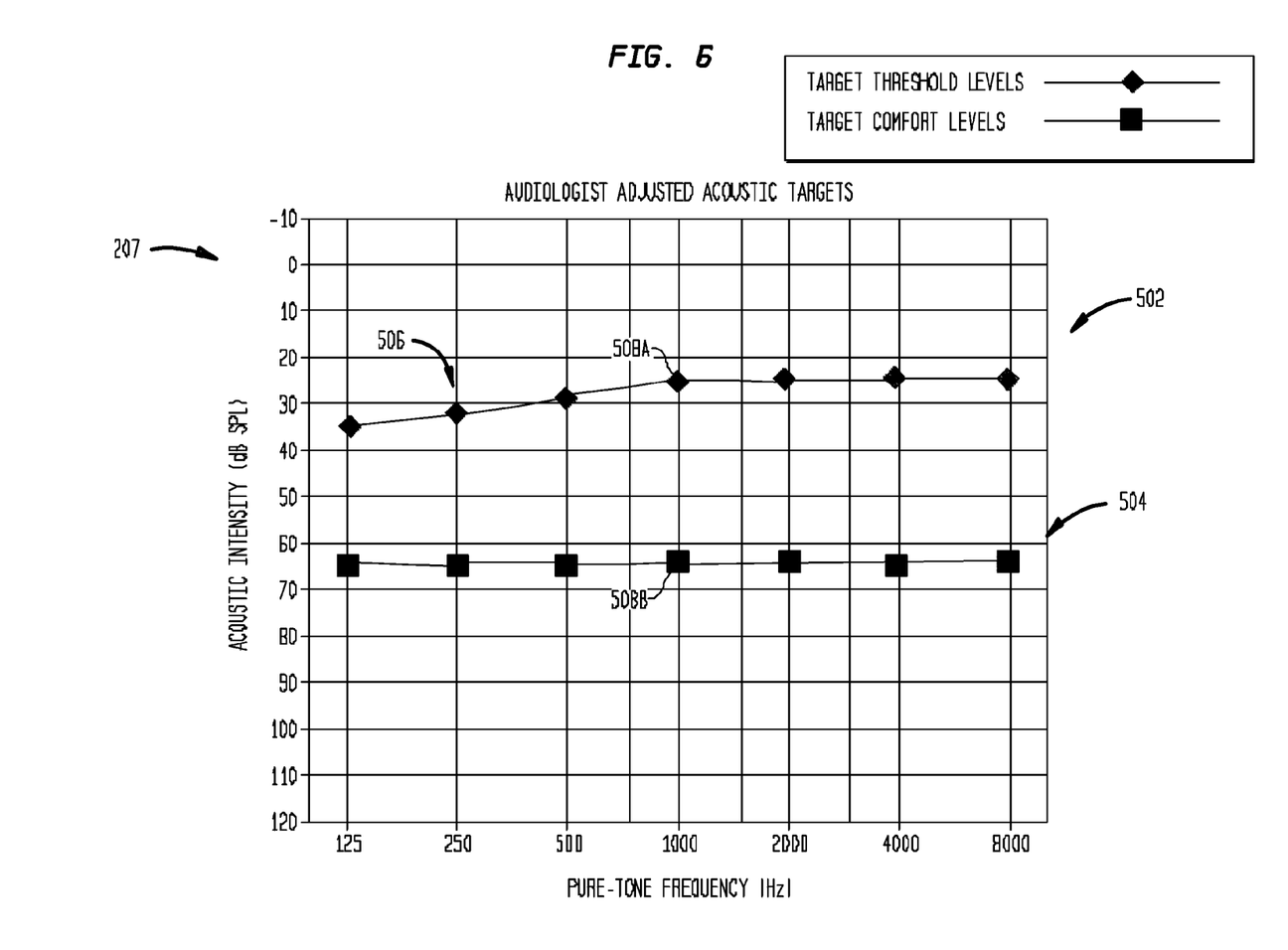
FIG. 6 is the exemplary target audiogram illustrated in FIG. 5 subsequent to when a third party adjusts acoustic targets, in accordance with embodiments of the present invention.

Target audiogram 207 illustrated in FIGS. 5 and 6 illustrates measurement data or other data in the acoustic domain; that is, using acoustic-based data which is the form commonly used by audiologists to fit hearing aids. In embodiments, each acoustic target 508A and 508B is displayed in target audiogram 207 at an acoustic signal intensity and frequency. In accordance with embodiments of the present invention, any measure or representation of intensity, such as Watts/square meter, decibels, etc, may used in target audiogram 207. In specific embodiments of the present invention, the intensities of acoustic targets 508A and 508B are specified in dB SPL; that is, dB with referenced to a fixed level, or dB HL; that is, dB referenced to normal hearing, depending on the preferences of third party 202. As such, external device 204 may have the ability to provide target audiograms in either dB HL or dB SPL or in any other measure or representation of intensity.

As shown in FIG. 5, in certain embodiments, at the commencement of the fitting procedure target audiogram 207 includes a plurality of acoustic targets 508 set at default acoustic intensities and frequencies. These default acoustic intensities may be, for example, ideal or preferred acoustic intensities at which it is desirable for a recipient to hear a sound. For example, external device 204 may initially display 25 dB for target thresholds. In the illustrative embodiments, target audiogram 207 comprises seven pure-tone octave frequencies at which acoustic targets 508 are set by third party 202. It should be appreciated that more or less frequencies may also be used. As shown, the third party may set multiple acoustic targets 508 for each frequency. For example, the audiologist may set target thresholds 502 and target comforts 504 for each frequency.

Third party 202 may adjust the acoustic intensity levels of acoustic targets from the default levels depending on the listening needs of the recipient, typical usage environment, etc. These adjustments may be made using, for example, control inputs 210 described above. As shown in FIG. 6, when audiologist adjusts the intensities, the symbols representing the acoustic target move up or down on the screen. In the illustrative embodiment of FIG. 6, third party has adjusted target threshold levels 606 and 608A in the lower frequency range by increasing the acoustic intensity thereof. This is shown by the movement of the symbols in lower frequency range 606 and 608A in FIG. 6. An increase in the intensity of target threshold levels in lower frequency 606 would be desirable, for example, if the recipient's typical use environment includes low-intensity and low-frequency background noise.

As noted above, in embodiments of FIGS. 5 and 6 describe threshold and comfort levels measured at a target frequency. In alternative embodiments of the present invention, one of either threshold or comfort levels or any level therebetween. The level measured to evoke the desired percept is then stored in the memory of the hearing device as described above.

As described above, external device 204 measures the output levels corresponding to each acoustic target 508 that will result in a desired percept when an acoustic signal is presented to hearing device 100 at the target frequency and intensity. In some embodiments, indications of these measured levels may optionally be provided from electronic unit 114 to external device 204 for display to third party 202. Rather than displaying the measured mV levels directly to third party 202, external device may display a representation of the output in a user friendly format which does not require an understanding of the output levels.

It should appreciated that target audiogram 207 may be displayed on any suitable apparatus or media. Similarly, although embodiments of the present invention are discussed herein with reference to target audiogram 207, other presentations of frequency-gain relationships are feasible. For example, it should appreciated that such frequency-gain relationships may be represented in other forms including, but not limited to, bar graphs, tables, histograms, drop-down menus, radio buttons, text boxes, or any other method for displaying such data.

In some embodiments, the control settings are configured to reduce effects of resonances occurring in the hearing device. The external device may be operable to measure resonance frequencies by a continuous or discontinuous sweeping of frequencies within a certain frequency band, and preferably over a total frequency range including all frequencies normally perceivable by the human ear. In some embodiments, the hearing device has a noise generator to perform these sweeps. In other embodiments, a sine generator performs the frequency sweep. As one of ordinary skill in the art would appreciate, either of these devices or any other suitable device may be used to determine the resonance frequencies. Typically, in the present embodiment, the resonance frequencies occur at about 700 to 800 Hz; but they may occur at any frequency. As one of ordinary skill in the art would appreciate, these data are then stored in the memory unit and a peak finder function may be used to determine where the resonance occurs in each frequency. A resonance notch filter (anti peak, band stop) may then be set to reduce the effects of the resonance frequencies. The present system allows the recipient or a third party to use an external device to control the setting of the resonance notch filter.

In some embodiments, the control settings are configured to control a feedback management system. That is, a system configured to cancel or reduce feedback. As one of ordinary skill would appreciate, such a system may be used to increase audibility of the hearing device by allowing increased amplification using signal processing methods. For example, a software application may be used to determine the level of the feedback management in use and thus, determine how much additional amplification may be added before reaching the amplification limitations of the hearing device. The present system allows the recipient or a third party to use an external device to control the setting of the feedback management system.

In some embodiments, the control settings are configured to control a noise reduction system. In some embodiments, a "beam former" is used to reduce or eliminate sounds from certain angles. In another embodiment, a modulation index calculation may be performed where signals with low modulation are reduced or removed. The present system allows the recipient or a third party to use an external device to control the setting of the noise reduction system.

In some embodiments, the control settings control the use and volume of an alarm signal. The alarm signal may produce an audible beep or other warning signal. The control settings may control the audible signal based on the real world environment. The hearing device may be configured to determine the background noise and adjust the alarm signal to compensate for the background noise. The hearing device may automatically determine the level of the background noise or the recipient may manual check the level of the background noise by engaging a switch or button or in any other manner. Thus, in a quiet environment, the control settings may reduce the level of the audible alarm signal, compared to the audible level in a loud environment. In some embodiments, the alarm signal has a minimum loudness level for use in very quiet environments and a maximum loudness level for use in very loud environments. Additionally, the control settings may set the alarm levels for each environment with an offset of, for example 6 dB louder than the environment. Further, in one embodiment, the control settings are configured to select a frequency of the alarm signal, so that a frequency is selected within a frequency band in which the recipient has relatively good hearing abilities.

The control settings may control any suitable or desired variety of parameters within the hearing device. One of ordinary skill in the art would understand that the control settings would be operable to 1) control the compression at various frequencies, 2) to control the maximum power output at various frequencies, i.e. a restriction to the maximum power output that is related to the patient's ability to hear at each frequency or frequency band; 3) control directivity of the sound perceived by the microphones of the hearing device, i.e. if the received sound is received mainly from the front, or in all directions; and 4) control the speech enhancement at different frequencies.

As noted above, the external devices described herein include interactive software and computer hardware to configure individualized recipient control settings. Therefore, the embodiments described herein may be carried out on a computer readable medium having computer-executable instructions for executing the recipient customization of the bone conducting hearing device.

The customization process performed separately for both sides of the recipient's head. In such an embodiment, the customization processes may be performed simultaneously or sequentially.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart there from.

What is claimed is:

1. A method for recipient customization of a bone conducting hearing device, comprising: attaching the bone conducting hearing device to a recipient;
generating at least one control setting with an external device;
transmitting the at least one control setting to the bone conducting hearing device; and
storing the at least one control setting in a memory device in the bone conducting hearing device.

2. The method of claim 1, wherein the step of generating the at least one control setting includes generating a plurality of settings each having a different amplification at a respective frequency.

3. The method of claim 1, further comprising:
generating an audiogram that measures bone conduction threshold values.

4. The method of claim 3, wherein the hearing device is configured to generate vibrations useable for measurement of the bone conduction threshold values.

5. The method of claim 1, further comprising:
measuring vibrations transmitted to the recipient's skull bone by the bone conducting hearing device for a plurality of frequencies; and
the generating step comprises:
generating a plurality of control settings each having a different amplification for each said plurality of different frequencies.

6. The method of claim 5, wherein the measuring step includes measuring resonance frequencies, wherein the plurality of control settings are adapted to dampen said resonance frequencies.

7. The method of claim 1, further comprising:
altering the control settings based on the subjective percept of the recipient; and
storing said altered control settings in the bone conducting hearing device.

8. The method of claim 1, wherein the generating step includes generating a plurality of control settings, each said plurality of control settings configured to be altered by the external device.

9. The method of claim 1, wherein the at least one control setting controls at least one of frequency amplification, maximum power output at a plurality of frequencies, frequency compression, noise reduction, directivity and speech enhancement at a plurality of frequencies.

10. The method of claim 1, wherein the at least one control setting controls the volume of an alarm signal.

11. The method claim 1, wherein the storing step includes storing the at least one control setting in non-volatile memory.

12. A bone conducting hearing device, comprising:
a microphone configured to generate a signal;
a signal processing unit configured to amplify the signal from the microphone;
a vibrator configured to convert the amplified signal into vibrations;
an interface configured to allow the hearing device to communicate with an external device that is external to the hearing device; and
at least one memory unit for storing control data for controlling the signal processing unit;
wherein the interface is adapted to receive control signals from the external device for generating vibrations in the vibrator at a plurality of predetermined frequencies, and to receive control settings for the signal processing unit for storing in said memory unit to reproduce the vibrations at each said predetermined frequency.

13. The hearing device of claim 12, wherein the at least one memory unit is configured to store a plurality of control settings, each control setting having a different amplification for each of a plurality of different frequencies.

14. The hearing device of claim 12, wherein the at least one memory unit is configured to store a control setting that controls the volume of an alarm signal.

15. The hearing device of claim 12, wherein the at least one memory unit includes a first memory unit for short-term storage of control data, and a second memory unit for long-term storage of control data, said second memory unit being a non-volatile memory.

16. The hearing device of claim 12, wherein the signal processing means includes electronic filters.

17. The hearing device of claim 12, wherein the interface is configured to allow bidirectional communication between the hearing device and the external device.

18. A non-transitory computer readable medium having computer-executable instructions for executing
recipient customization of a bone conducting hearing device, the computer-executable instructions performing steps comprising: establishing communication between the bone conducting hearing device and an external control device; determining measurement data related to the recipient's ability to perceive sound at a predetermined frequency;
generating at least one control setting for a signal processing unit based on said bone conduction threshold; and
transmitting said at least one control setting to the hearing device.

19. The computer readable medium of claim 18, wherein the step of
determining measurement data includes determining the recipient's threshold level at the predetermined frequency.

20. The computer readable medium of claim 19, wherein the steps of
determining measurement data includes determining the recipient's threshold level at a plurality of predetermined frequencies;
generating at least one control setting includes generating a plurality of control settings for each said plurality of predetermined frequencies; and
transmitting said at least one control setting includes transmitting said a plurality of control settings to the hearing device.

* * * * *